US011554218B2

(12) United States Patent
Keadle

(10) Patent No.: US 11,554,218 B2
(45) Date of Patent: Jan. 17, 2023

(54) MIXING VIAL

(71) Applicant: Balanced Pharma Incorporated, Cornelius, NC (US)

(72) Inventor: John Scott Keadle, Cornelius, NC (US)

(73) Assignee: Balanced Pharma Incorporated, Cornelius, NC (US)

( * ) Notice: Subject to any disclaimer, the term of this patent is extended or adjusted under 35 U.S.C. 154(b) by 0 days.

(21) Appl. No.: 17/742,100

(22) Filed: May 11, 2022

(65) Prior Publication Data
US 2022/0265933 A1    Aug. 25, 2022

Related U.S. Application Data

(63) Continuation of application No. 17/722,016, filed on Apr. 15, 2022, which is a continuation of application No. 15/860,141, filed on Jan. 2, 2018, now Pat. No. 11,305,064.

(60) Provisional application No. 62/441,431, filed on Jan. 1, 2017.

(51) Int. Cl.
| | |
|---|---|
| *A61M 5/24* | (2006.01) |
| *A61J 1/20* | (2006.01) |
| *A61M 5/19* | (2006.01) |
| *A61M 5/315* | (2006.01) |
| *A61M 5/28* | (2006.01) |

(52) U.S. Cl.
CPC .......... *A61M 5/2448* (2013.01); *A61J 1/2041* (2015.05); *A61J 1/2093* (2013.01); *A61M 5/19* (2013.01); *A61M 5/284* (2013.01); *A61M 5/31596* (2013.01); *A61M 2005/2462* (2013.01); *A61M 2005/287* (2013.01)

(58) Field of Classification Search
CPC .... A61M 5/19; A61M 5/2422; A61M 5/2448; A61M 5/284; A61M 5/31596; A61M 5/3294; A61M 2005/2462; A61M 2005/287; A61J 1/2041; A61J 1/2093
See application file for complete search history.

(56) References Cited

U.S. PATENT DOCUMENTS

| | | |
|---|---|---|
| 2,238,582 A | 4/1941 | Dickinson |
| 2,244,969 A | 6/1941 | Smith |
| 2,705,956 A | 4/1955 | McLaughlin |
| 3,347,410 A | 10/1967 | Gilbert |

(Continued)

FOREIGN PATENT DOCUMENTS

| | | |
|---|---|---|
| EP | 2399564 A1 | 12/2011 |
| EP | 2407194 A1 | 1/2012 |

(Continued)

OTHER PUBLICATIONS

International Search Report and Written Opinion in connection to PCT/US2020/055950, dated Jan. 29, 2021.

(Continued)

*Primary Examiner* — Shefali D Patel
(74) *Attorney, Agent, or Firm* — Meunier Carlin & Curfman LLC

(57) ABSTRACT

A mixing vial having a hollow interior chamber with a tubular portion having distal and proximal open ends and a stopper positioned in sealing relationship in the tubular portion, the stopper having a hollow interior chamber with an open end and a dislodgeable plug positioned in and sealing the open end.

10 Claims, 5 Drawing Sheets

(56) References Cited

U.S. PATENT DOCUMENTS

| | | | |
|---|---|---|---|
| 4,041,945 A * | 8/1977 | Guiney | A61M 5/31596 |
| | | | 604/91 |
| 5,593,028 A | 1/1997 | Haber et al. | |
| 5,603,695 A | 2/1997 | Erickson | |
| 6,003,728 A | 12/1999 | Elliott | |
| 8,162,917 B2 | 4/2012 | Stepovich et al. | |
| 8,672,878 B2 | 3/2014 | Finke | |
| 8,911,395 B2 | 12/2014 | Just | |
| 8,974,407 B2 | 3/2015 | Finke | |
| 9,051,100 B2 | 6/2015 | Suzuki | |
| 9,055,992 B2 | 6/2015 | Larson | |
| 9,265,894 B2 | 2/2016 | Finke | |
| 9,616,176 B2 | 4/2017 | Just | |
| 2015/0165124 A1 | 6/2015 | Just | |

FOREIGN PATENT DOCUMENTS

| | | | | |
|---|---|---|---|---|
| GB | 430263 A * | 6/1935 | | A61M 5/284 |
| GB | 430263 A | 6/1935 | | |

OTHER PUBLICATIONS

International Preliminary Report on Patentability in connection to PCT/US2020/055950, dated Apr. 28, 2022.

\* cited by examiner

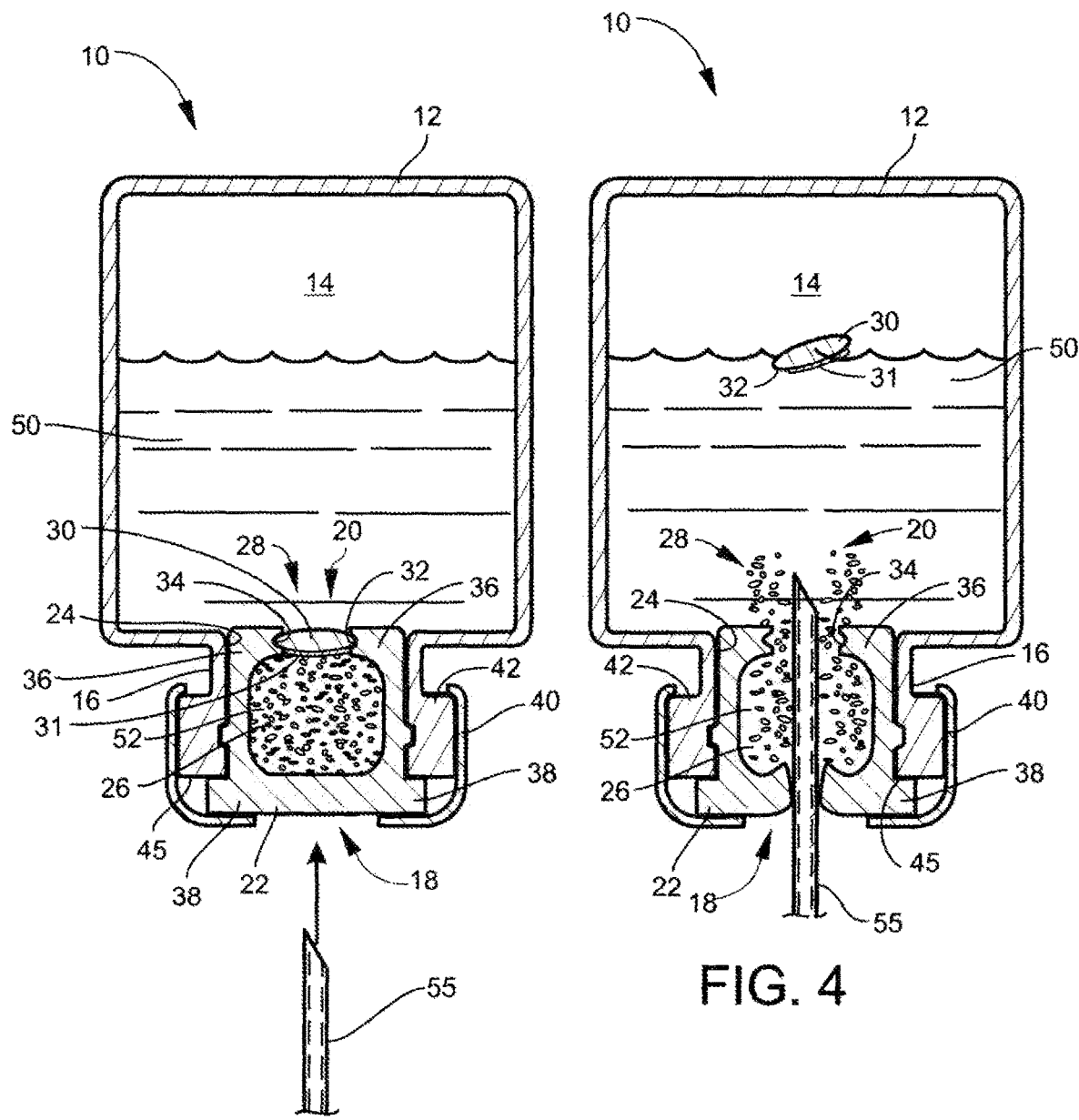

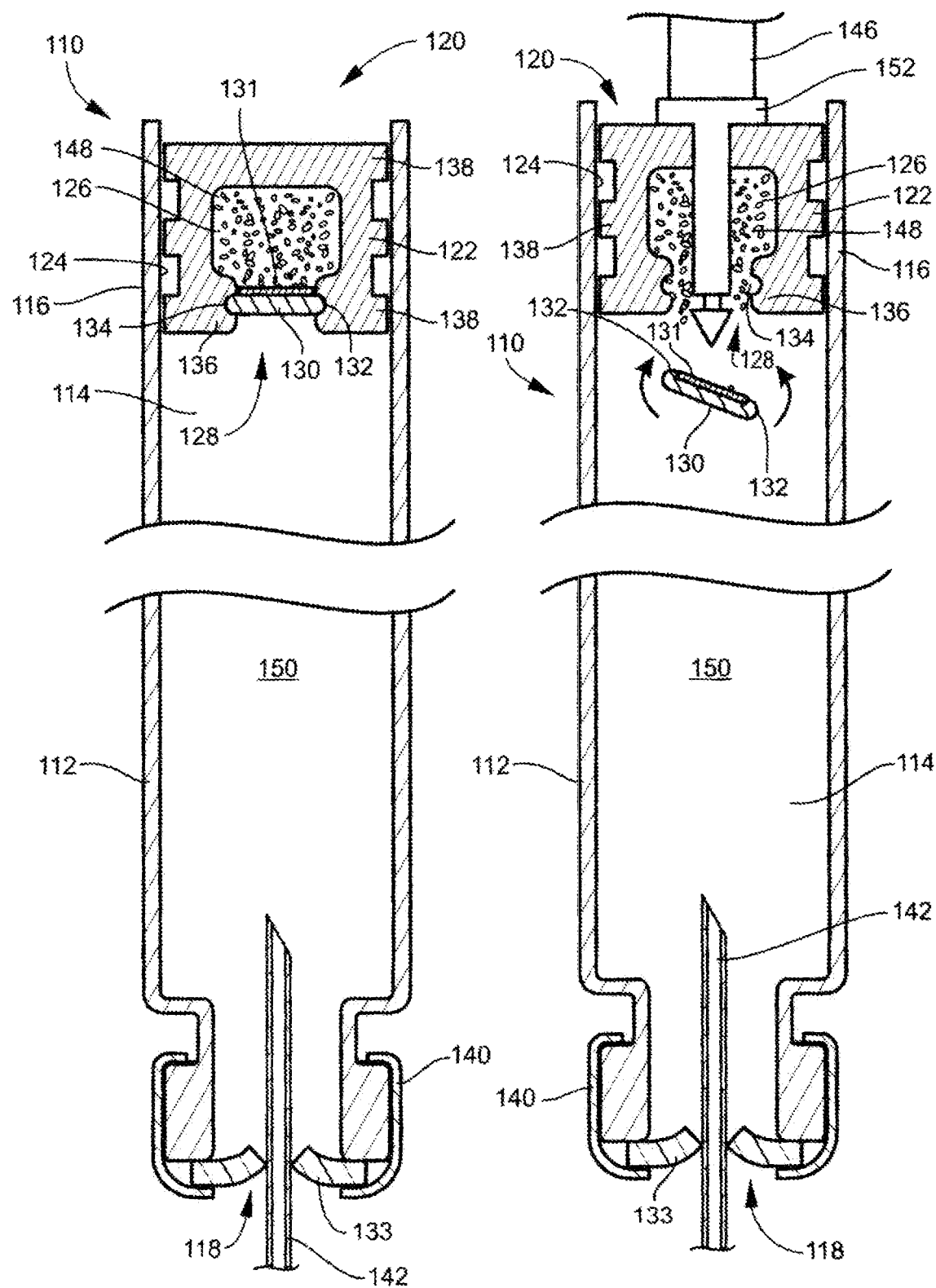

MIXING VIAL

CROSS-REFERENCE TO RELATED APPLICATIONS

This application is a continuation of U.S. application Ser. No. 17/722,016, filed Apr. 15, 2022, which is a continuation of U.S. application Ser. No. 15/860,141, filed Jan. 2, 2018, which claims the benefit of provisional patent application Ser. No. 10 62/441,431, filed Jan. 1, 2017, the content of which is incorporated herein by reference in its entirety.

FIELD OF THE INVENTION

This application relates to chemical vials. More particularly this application relates to medical and dental vials for storage, mixing and delivery of drugs such as buffered anesthetic solutions.

BACKGROUND OF THE INVENTION

For various reasons, some drugs must be stored and transported in two parts, and then mixed together just prior to administration. For example, steroid drugs in powder form are sometimes mixed with various vehicles just prior to injection and local anesthetics are sometimes mixed with NaHCO3 buffering solution just prior to injection.

In addition, some drugs require agitation immediately prior to injection, and therefore require headspace for effective agitation, while at the same time being susceptible to oxidative degradation which occurs during storage from the gas in the headspace. These drugs benefit from vials that eliminate headspace during storage, but allow headspace for agitation just prior to injection.

Local anesthetic solution exerts its effect by blocking transmission of the nerve signal in the area of the nerve where the solution has been deposited. Generally speaking anesthetic solutions must be acidified to an acid pH of about 4.0 (akin to vinegar) to obtain adequate shelf life. This acid solution is painful to the patient when injected, and is just one more reason that, people, don't like getting shots at the dentists' or physicians' office. In addition, the drug does not exert any effect at this low "storage" pH, so the patient must wait several minutes after injection before the numbness begins, while their body slowly brings the pH up to that of the body tissues, which is about 7.4.

Overwhelming evidence demonstrates that raising the pH of the anesthetic to a pH closer to neutral just prior to injection ("buffering") greatly decreases the pain associated with injection, as well as the latency of the anesthetic effect. Because of this, many inventors over several decades have attempted to help make buffering a widespread practice in both dentistry and medicine, but at present no method has been satisfactory fora number of reasons.

Sodium bicarbonate (NaHCO3) in an 8.4% aqueous solution is the most common solution used to buffer anesthetic. The NaHCO3 solution and the local anesthetic solution are typically mixed in a ratio of about 9 parts anesthetic to 1 part NaHCO3 solution.

When physicians, such as dermatologists and plastic surgeons, buffer their anesthetic, they first draw anesthetic solution into their syringe from a vial, and then add NaHCO3 solution to the syringe by drawing it from a separate vial. The unused anesthetic and NaHCO3 solutions, in their respective vials, along with the needle and syringe, must be discarded after each patient. This protocol typically wastes more than 90% of the NaHCO3, and two vials are required. In addition, the mixing protocol is subject to human error and has resulted in protocol breaches, including improper drug ratios, sterility breaches, and intentional "re-use" of single-patient drug vials on other patients, with resulting adverse medical outcomes. This method is also somewhat cumbersome, time-consuming, and uneconomical. However, despite the risk, and the cost in time and money, many physicians buffer their anesthetic, as it makes a significant difference in the patient's comfort when performed properly.

It would be preferable to have a system for the physician to draw and mix anesthetic medications using only one vial. Drawing from one vial instead of two would save valuable time, make the process safer, save the costs of the extra vial and the excess buffer solution, result in more widespread use of buffering, and increase patient comfort.

In the oral environment, because of the special need for dexterity and the likelihood of multiple injections on the same patient, dentists typically inject the anesthetic solution with a reusable hand-held metal syringe, which has evolved and consolidated into a single design that accounts for almost all syringes in use in dentistry and oral surgery. This syringe is used in conjunction with a disposable hollow injection needle which is attached to the syringe and a specialized glass drug vial called a "cartridge" or "carpule" of anesthetic solution, which is placed into the syringe. As the cartridge is placed into the syringe, the cartridge is pierced by the back end of the needle, so that solution can flow out and through the needle. The cartridge has a piston that is driven by a pushrod on the syringe, so that when the dentist pushes on the pushrod the piston drives the solution through the attached needle.

The cartridge has the shape of an elongated barrel. The cartridge is sealed on one end with a puck shaped elastomeric membrane that is fastened with a crimped metal cap in the manner typical of most glass drug vials A notable and important difference between a dental cartridge and a typical drug vial is the size. A dental cartridge volume is typically less than 2 ml, due mainly to limitations imposed by the syringe fitting in the operator's hand and its use in the mouth, whereas a typical drug vial has a volume of 10-100 ml.

Dentists who buffer their anesthetic typically use one of two commercially available systems. Both of these systems add considerable time and expense to the procedure. The ongoing product cost per injection of the commercially available systems is many times that of an unbuffered protocol. One system for dentists requires dentists to use a syringe/needle combination that is very different than the standard system that is ubiquitous in the industry. This system also requires a countertop device that contains both anesthetic solution and NaHCO3 solution in separate vials and is used to load the disposable syringe/needle combination. This is time consuming, expensive, and its use is subject to operator error and breaches of sterile and pharmacological protocol.

Another system for dentists utilizes an injector that introduces NaHCO3 into the standard dental cartridge. This system requires that each cartridge be separately loaded with NaHCO3, which is time consuming, and in some states legally prohibited except by licensed pharmacists. In addition, this system causes a significant loss of available drug volume in the cartridge as well as being subject to operator error and breaches of sterile and pharmacological protocol.

In spite of their disadvantages, both systems have found a limited market, demonstrating that buffering is very desirable from both a dentist's and a dental patient's perspective.

Making the buffering process less time consuming, less expensive, safer, and more similar to current surgical protocol would result in more widespread use for the benefit of both patient and dentist.

In the case of steroid drugs, physicians typically are provided with a special glass vial that has been partitioned into two chambers. The glass vial is provided with a plunger mechanism that the physician manually depresses to mix the contents of the chambers. The "Act-O-Vial" is typical of these special vials. The Act-O-Vial consists of seven parts and requires a specially shaped glass vial and apparatus.

The Act-O-Vial and similar special vials are also used in conjunction with drugs which require headspace for agitation, but benefit from a lack of headspace during storage. In this case, the fluid in the first chamber is stored without headspace, and then utilizes the headspace in the second chamber to permit agitation.

There remains a need to provide a less time consuming and less expensive method for in situ mixing or agitation of drugs, notably including the buffering of local anesthetic and the mixing of steroids for injection. Accordingly it is desired to provide various embodiments of the present invention as follows: to provide a mixing cartridge suited for use with dental syringes which may be manufactured more simply, using an extruded hollow glass tube that is cut to length, rather than a complicated form requiring each cartridge to be individually blown around a mandrel; to simplify the filling and sealing of the dental cartridge by requiring fewer and simpler parts; to eliminate the use of metal crimped caps for sealing, along with the metal dirt and dust which contaminates the clean or sterile assembly lines required for the manufacture of dental cartridges; to provide maximal interior volume to contain a drug; to facilitate the ability to eliminate gaseous headspace and the associated oxidative degradation of the drug in a dental cartridge; to provide a mixing dental cartridge that allows maximum interior volume for drug storage while minimizing breakage; to provide mixing or agitation of drugs used in medicine or dentistry using a minimum of simple parts; to reduce the possibility of operator error and breaches in sterile or pharmacological protocol when mixing drugs; to provide a mixing vial stopper which may be used with the typical medical vial and the typical crimped sealing cap, rather than requiring a specially shaped vial that is difficult to manufacture or a multipart sealing mechanism; to save time and cost, to facilitate accurate proportioning of materials to be mixed and avoid operator error; to make widespread the use of local anesthetic buffering; to reduce pain and waiting time in the administration of local anesthesia in medical and dental offices.

Other advantages of one or more aspects will be apparent from the following disclosure and claims taken in conjunction with the accompanying drawings.

SUMMARY OF THE INVENTION

A mixing vial has a unitary hollow chambered vial stopper with a dislodgeable plug separating the hollow stopper chamber from the vial chamber. The plug may be dislodged to allow mixing of the contents of the stopper chamber and the vial chamber or agitation of a drug in the headspace created.

BRIEF DESCRIPTION OF THE DRAWINGS

FIG. 3 is an exploded, sectional view, in vertical section, of an embodiment of a mixing vial of the present invention with its dislodgeable plug in sealing position and a needle, broken away;

FIG. 4 is a sectional view, in vertical section, of an embodiment of FIG. 3 with its plug dislodged and a needle, shown broken away, the needle having been inserted into the vial to dislodge the plug;

FIG. 8 is a sectional view of an embodiment of a mixing vial of the present invention in cartridge form with a needle inserted therein, the needle shown broken away;

FIG. 9 is a sectional view of the embodiment of FIG. 8, with a needle inserted therein, the needle shown broken away, after the harpoon-plunger of the syringe has been inserted into and through the hollow chambered piston and dislodged the plug

DESCRIPTION OF THE INVENTION

Figure 2:
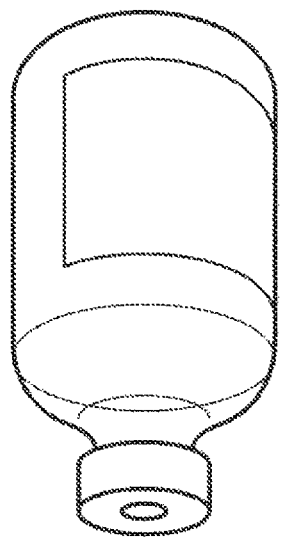
FIG. 2 is a perspective view of a conventional vial having a single chamber.
Figure 1:
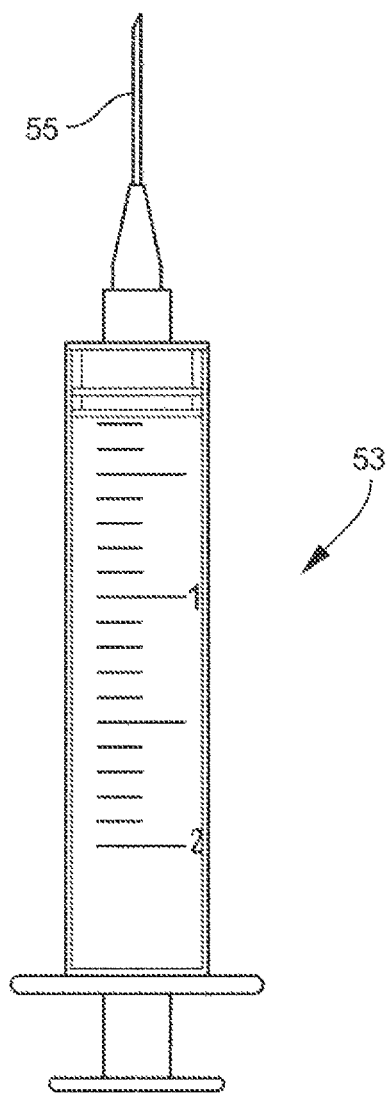
FIG. 1 is a side elevation of a conventional needle/syringe apparatus for use in combination with a vial of the present invention.

Now referring to the drawings, a conventional prior art syringe/needle apparatus is illustrated in FIG. 1 while a conventional prior art vial is illustrated in FIG. 2. The syringe/needle apparatus of FIG. 1 is suitable for use in conjunction with an embodiment of the mixing vial of the present invention as will be described in more detail in the following disclosure. The conventional prior art vial does not have dual chambers or a plug and is shown for illustrative purposes.

FIGS. 3 and 4 illustrate a mixing vial of the present invention which is indicated by the numeral 10. Mixing vial 10 provides the ability for physicians to buffer local anesthetic prior to injection in a manner that is economically feasible, is not excessively time-consuming, does not interfere with established surgical protocol, and does not require new or unfamiliar surgical equipment.

Broadly speaking, mixing vial 10 is a generally barrel shaped vessel 12 having a hollow interior chamber 14 and neck 16 having distal and proximal open ends, 18 and 20. An elastomeric, chambered stopper 22 is positioned in neck 16 and is in sealing relationship with interior facing wall 24 of neck 16.

Chambered stopper 22 has a hollow interior chamber 26 and an open proximal end 28 with a dislodgeable plug 30 positioned in and sealing said open end 28. Thus, annular edge 32 of plug 30 is tightly fit into annular groove 34 in radially inwardly extending stopper flange 36 of stopper 22. Vessel 12 may be made of glass, plastic or any other material suitable for use consistent with the purpose of the present invention. Stopper 22 may be made of elastomeric plastic or rubber material, including the typical vial stopper material in present use, which will seal well with adjacent surfaces. Plug 30 may be made of PTFE, or any material or combination of materials suitable for sealing with stopper 22 and resisting penetration of the needle. For instance, plug 30 may have an elastomeric body and edge, with a PTFE strike plate 31 attached to the needle side to prevent needle penetration.

Stopper 22 has a radially outwardly extending annular flange 38 and is retained in position on neck 16 by metal clip 40 which clips onto annular shoulder 42 on neck 16 and compresses flange 38 against distal face 45 of neck 16.

As shown in FIGS. 3 and 4, interior chamber 14 of vessel 12 contains solution 50, for example, a local anesthetic solution, or a physiologic saline solution. Interior chamber 26 of stopper 22 contains a powder 52, for example, NaHCO3, or a powdered steroid medication.

In operation, the mixing vial 10 of the present invention is used in accordance with the following method. First, a mixing vial of the present invention is provided and its two chambers filled with suitable drugs or other materials which are desired to be kept separate and then mixed just before injection. Then, the vial is inverted and, using a typical disposable medical syringe 53 as illustrated in FIG. 1, the physician inserts the Syringe Needle 55 into the chambered stopper 22 as illustrated in FIGS. 3 and 4. The physician must make certain that the Syringe Needle passes through chamber 26 of stopper 22 and dislodges plug 30 into the chamber 14 of mixing vial 10. The dislodged plug 30 may float to the top of the mixed solution, or alternatively be configured to stay in solution to aid in mixing the drugs. Also, vial 10 may be shaken to assist in mixing. Coloring or clouding reagents may be added to either chamber to provide visual indication of mixing or premature seal failure. The form of the Chambered Vial Stopper assembly allows elimination of headspace gas in one or the other of the chambers. The physician withdraws the mixed drug solution from the inverted vial into the syringe apparatus and administers it to the patient in the typical manner.

Figures 5, 6, 7:
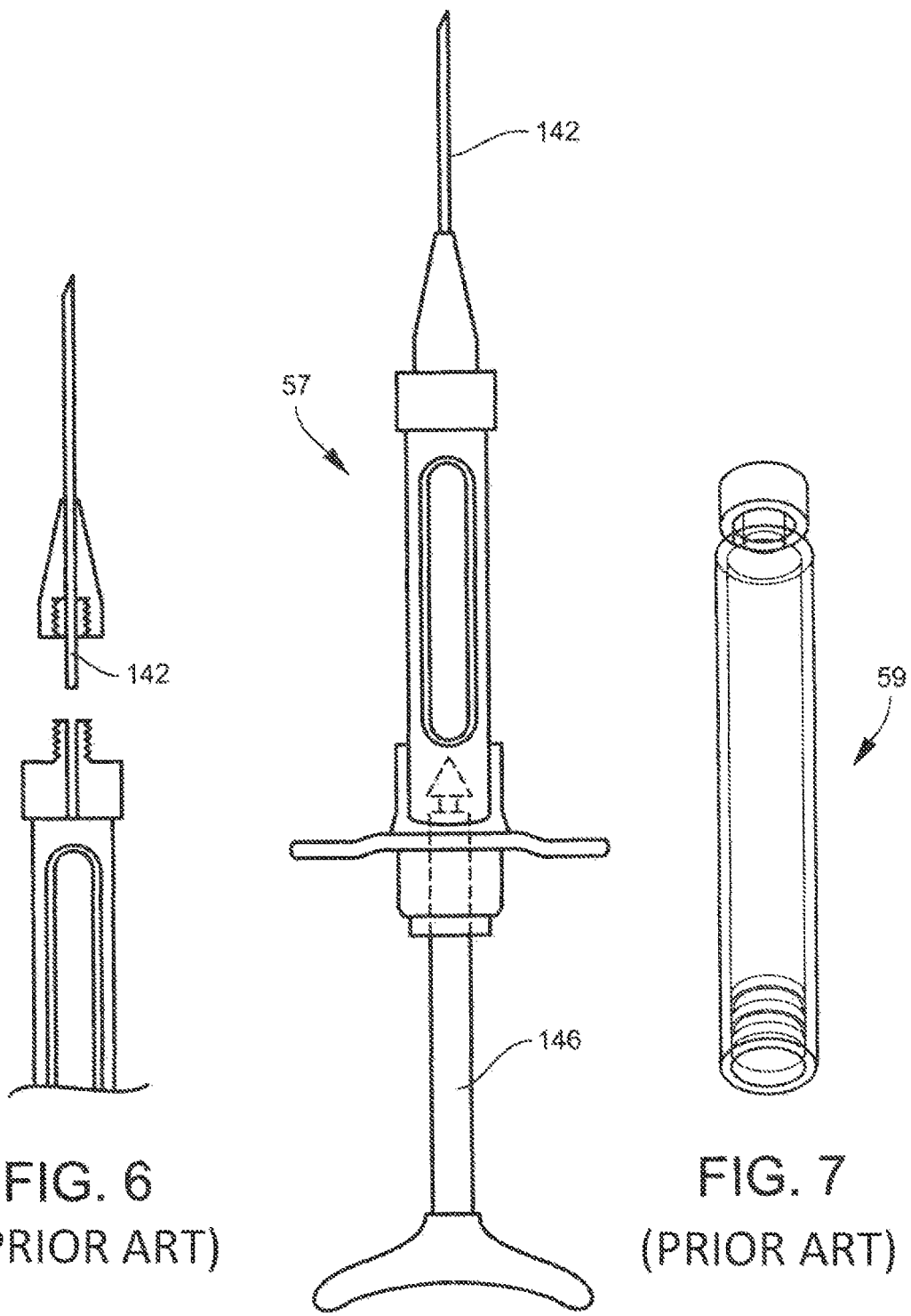
FIG. 5 is a side elevation of a conventional dental cartridge needle/syringe apparatus for use in combination with a cartridge of the present invention.
FIG. 6 is an exploded sectional view, broken away, of the conventional dental cartridge needle/syringe apparatus of FIG. 5.
FIG. 7 is a perspective view of a conventional dental cartridge having a single chamber.

Now referring to FIGS. 5 and 6 a conventional syringe 57 for use with vials configured as cartridges such as the conventional dental cartridge 59 shown in FIG. 7 is illustrated. The conventional cartridge syringe is also useful for use with a cartridge style mixing vial of the present invention as further described below.

As shown in FIGS. 8 and 9, mixing vial 110 is in the form of a cartridge and has a generally barrel shaped vessel 112 having a hollow interior chamber 114 and neck 116, and having distal and proximal open ends, 118 and 120. Neck 116 is a portion of vessel 112 at the proximal end thereof and is simply an extension of the vessels tubular structure, the wall thickness, and diameter of vessel 112 not being reduced for neck 116. An elastomeric, chambered stopper-piston 122 is positioned in neck 116 and is in sealing relationship with interior facing wall 124 of neck 116.

Chambered stopper-piston 122 has a hollow interior chamber 126 and an open distal end 128 with a dislodgeable plug 130 positioned in and sealing said open end 128. Thus, annular edge 132 of plug 30 is tightly fit into annular groove 134 in radially inwardly extending stopper flange 136 of stopper 122. Vessel 112 may be made of glass, plastic or any other material suitable for use consistent with the purpose of the present invention. Stopper-piston 122 may be made of elastomeric plastic or rubber material which will seal well with adjacent surfaces. Plug 130 may be made of PTFE, or any material or combination of materials suitable for sealing with stopper-piston 122 and resisting penetration of the harpoon-plunger 146. For instance, plug 130 may have an elastomeric body and edge, with a PTFE strike plate 131 attached to the harpoon side to prevent harpoon penetration. Plug 130 may take the form of a sphere, convex disc, or other forms, and may be used for agitation of the chemicals to be mixed. Stopper-piston 122 may have annular ribs 138 or other aids for sealing and stability.

Open distal end 118 of vessel 112 is sealed by rubber sealing cap 133 which is held in place by metal clip 140.

In use, it is intended that cap 133 will be pierced by needle 142, as illustrated in FIG. 9, when medical mixing vial, or cartridge, 110 is placed in syringe 57. Then, pushrod 146 is moved downwardly to first pierce stopper 122 and then dislodge plug 130 as illustrated in FIG. 9. Chemical reagent 148 such as buffering material in chamber 126 of stopper 122 is thus allowed to mix with solution 150 in chamber 114. The mixture of drugs is then injected into a patient by manipulating pushrod 146 further downwardly, with shoulder 152 of pushrod 146 pushing against stopper 122 to push stopper 122 downwardly to act as a piston, sliding down vessel 112 and hydraulically expelling the liquid therein through needle 142.

Figure 10:
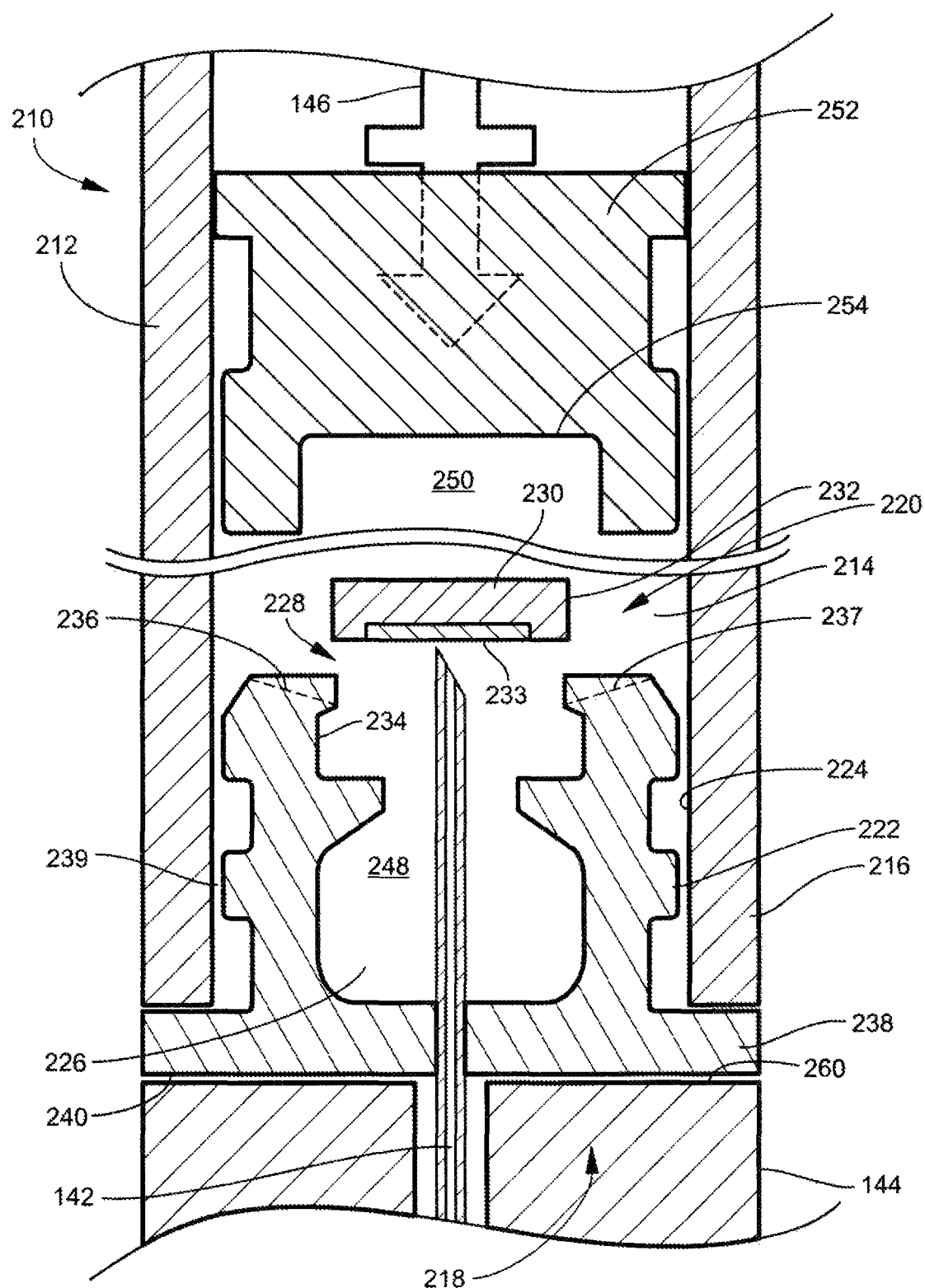
FIG. 10 is a sectional view, broken away, of an embodiment of a mixing vial of the present invention in cartridge form with a needle inserted therein, the needle having dislodged the plug to effect mixing of the two chambers' contents.

Another embodiment is shown in FIG. 10. As shown in FIG. 10, mixing vial 210 is in the general form of a syringe cartridge and has a generally barrel shaped vessel 212 having a hollow interior chamber 214 and neck 216 having distal and proximal open ends, 218 and 220. Neck 216 is a portion of vessel 212 at the distal end thereof and is simply an extension of the vessels tubular structure, as the wall thickness and diameter of vessel 212 are not changed for neck 216. An elastomeric, chambered stopper 222 is positioned in neck 216 and is in sealing relationship with interior facing wall 224 of neck 216. Stopper 222 has a radially outwardly extending annular flange 238 and ribs 239 and 241 and is retained in position in neck 216 during storage and transport by friction with vessel 212. During use, retention of stopper 222 in neck 216 is insured by proximally facing face 260 of syringe 57.

Chambered stopper 222 has a hollow interior chamber 226 and an open proximal end 228 with a dislodgeable plug 230 positioned in and sealing said open end 228. Thus, annular edge 232 of plug 230 is tightly fit into annular groove 234 in radially inwardly extending stopper flange 236 of stopper 222. The proximal face of stopper flange 236 may have radial grooves 237 to provide flow should plug 230 become lodged against proximal face of flange 236 after dislodgement from groove 234.

Vessel 212 may be made of glass, plastic or any other material suitable for use consistent with the purpose of the present invention. Stopper 222 may be made of an elastomeric plastic or rubber material, including the typical vial stopper material in present use, which will seal well with adjacent surfaces. Plug 230 may be made of PTFE, or any material or combination of materials suitable for sealing with stopper 222 and resisting penetration of the needle. For instance, plug 230 may have an elastomeric body and edge, with a PTFE strike plate 233 attached to the needle side to prevent needle penetration. Stopper 222 may have annular ribs or other sealing and retentive aids. Neck 216 may have inwardly facing grooves, ledges, or flanges to aid in sealing and retention of stopper 222.

Open proximal end 220 of vessel 212 is sealed by piston 252. Piston 252 is shown with a hollow recess 254 in the distal face which adds available volume inside the interior chamber 214 of the mixing vial 210 and prevents damage to the proximal end of needle 142 as piston 252 translates distally.

In use, it is intended that stopper 222 will be pierced by needle 142, as illustrated in FIG. 10 when mixing vial, or cartridge, 210 is placed in syringe 144. Then, needle 142 dislodges plug 230 from stopper 222, as proximally facing syringe face 260 abuts stopper distal face 240 and prevents hydraulic dislodgement. Chemical reagent 248 such as buffering material in chamber 226 of stopper 222 is thus allowed to mix with solution 250 such as local anesthetic in chamber 214. The mixture is then injected into a patient by manipulating syringe pushrod 46 distally against piston 252, hydraulically expelling the liquid through needle 142.

While embodiments of the present invention have been disclosed, it will be appreciated by those skilled in the art that the invention is subject to variations and modifications and it is intended that the invention will be limited only by the following claims. For example, as alternatives to the embodiments disclosed, the vial may be of three or more chambers instead of two, allowing the mixing of more components. The vial may serve to enhance the in-situ mixing of chemicals in applications not specifically mentioned here or in applications not yet contemplated. The materials to be mixed in either chamber may be a solid, powdered solid, fluid, gas, or a mixture of any or all of the above. Coloring, clouding, or other reagents may be used to visually indicate mixing of the components or leakage of the seals between the chambers or the exterior. The plug, to be dislodged may be rigid, or mainly rigid with an elastic portion or mainly elastic with a rigid portion. The stopper may be elastic, or mainly elastic with a rigid portion, or mainly rigid with an elastic portion. Any of the parts may include features that improve, simplify, or shorten the manufacturing of those parts or improve, simplify, or shorten the assembling of the overall apparatus. Any of the parts or the overall apparatus may include features that improve the visual marketing appeal of the apparatus. The vessel or any part of the vessel, while described in the embodiments as having a generally circular cross-section in one plane, may have any other shape in cross-section that permits use.

What is claimed is:

1. A syringe system, the system comprising:
    a syringe including a body, a syringe needle, and an axially movable plunger, the syringe needle being statically coupled to a distal end of the body, the syringe needle having a distal end and a proximal end; and
    a mixing vial for use in the syringe, said mixing vial comprising:
        a vessel, the vessel comprising a hollow interior chamber with proximal and distal ends, a neck on the distal end of the hollow interior chamber of the vessel, the neck having distal and proximal open ends;
        a piston, the piston slidably positioned in the proximal end of said hollow interior chamber of the vessel;
        a stopper, the stopper including an open proximal end, a closed distal end opposite and spaced apart from the open proximal end, and at least one stopper side wall extending from the open proximal end to the closed distal end, wherein a hollow interior chamber is defined by the at least one stopper side wall and the closed distal end, the stopper being positioned in a sealing relationship with said neck; and
        a dislodgeable plug, the dislodgeable plug positioned in and sealing said open proximal end of the stopper, wherein the entire dislodgeable plug is fully dislodgeable as a single piece from the open proximal end of the stopper,
    wherein said stopper defines an inward facing annular groove that receives an edge of the dislodgeable plug, and
    wherein said dislodgeable plug is able to be dislodged by the syringe needle, and
    wherein the stopper further comprises a flange extending radially inwardly from the at least one stopper side wall of the stopper, wherein the flange has a first flange portion and a second flange portion axially spaced apart from the first flange portion,
  wherein the first flange portion is axially closer than the second flange portion to the open proximal end of the stopper, wherein the first flange portion and the second flange portion define the inward facing annular groove that receives the edge of the dislodgeable plug, wherein a radially inwardmost edge of the first flange portion has a first diameter and a radially inwardmost edge of the second flange portion has a second diameter,
  wherein the first diameter is larger than the second diameter;
  wherein, when the mixing vial is disposed in the syringe, the proximal end of the syringe needle is able to penetrate the closed distal end of the stopper, contact the dislodgeable plug, and fully dislodge the dislodgeable plug.

2. The system of claim 1, wherein the syringe comprises a dental syringe, the vessel comprising a shape that allows use with the dental syringe.

3. The system of claim 1, wherein the syringe needle pierces the stopper and dislodges the dislodgeable plug when the mixing vial is loaded into or placed in the syringe.

4. The system of claim 1, wherein the stopper further comprises a radially outwardly extending annular flange.

5. The system of claim 1, wherein the closed distal end of the stopper and the at least one stopper side wall are formed as a single piece.

6. The system of claim 1, wherein the vessel has an interior diameter that is uniform.

7. The system of claim 1, wherein said interior chamber of said vessel comprises an anesthetic, and said interior chamber of said stopper comprises a buffering reagent.

8. The system of claim 1, wherein the stopper comprises an elastomeric plastic or rubber.

9. The system of claim 1, wherein the piston comprises a hollow recess in a distal face.

10. The system of claim 1, wherein said interior chamber of said vessel comprises an anesthetic, and said interior chamber of said stopper comprises a buffering reagent, and the anesthetic and the buffering reagent are mixed.

* * * * *